(12) United States Patent
Gloeckle et al.

(10) Patent No.: US 9,404,845 B2
(45) Date of Patent: Aug. 2, 2016

(54) SENSOR FOR DETECTING THE QUALITY OF A FLUID

(75) Inventors: Markus Gloeckle, Stuttgart (DE); Andreas Fritsch, Waiblingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 253 days.

(21) Appl. No.: 14/119,491

(22) PCT Filed: Apr. 4, 2012

(86) PCT No.: PCT/EP2012/056186
§ 371 (c)(1),
(2), (4) Date: Feb. 11, 2014

(87) PCT Pub. No.: WO2012/159815
PCT Pub. Date: Nov. 29, 2012

(65) Prior Publication Data
US 2014/0150538 A1    Jun. 5, 2014

(30) Foreign Application Priority Data

May 26, 2011    (DE) .......................... 10 2011 076 496

(51) Int. Cl.
*G01N 13/04*    (2006.01)
*F01N 3/20*    (2006.01)
(Continued)

(52) U.S. Cl.
CPC .............. *G01N 13/04* (2013.01); *F01N 3/2066* (2013.01); *F01N 11/00* (2013.01); *G01L 19/06* (2013.01); *G01N 7/10* (2013.01); *F01N 2550/05* (2013.01); *F01N 2610/02* (2013.01);
(Continued)

(58) Field of Classification Search
CPC ... F01N 3/2066; F01N 11/00; F01N 2550/05; F01N 2610/02; F01N 2610/14; F01N 2610/1406; F01N 2900/1818; F01N 2610/148; G01L 19/06; G01N 13/04; G01N 7/10; Y02T 10/47; Y02T 10/24
USPC ......................................................... 73/64.47
See application file for complete search history.

(56) References Cited

U.S. PATENT DOCUMENTS 4,598,576 A * 7/1986 Goldsmith ............... G01N 7/10
73/31.07
4,666,672 A * 5/1987 Miller .................. G01N 21/643
422/82.07
(Continued)

FOREIGN PATENT DOCUMENTS

CN    2927035    7/2007
DE    21 63 640 A1    6/1973
(Continued)

OTHER PUBLICATIONS

International Search Report issued in PCT/EP2012/056186, dated Jun. 5, 2012.

*Primary Examiner* — Hezron E Williams
*Assistant Examiner* — Marrit Eyassu
(74) *Attorney, Agent, or Firm* — Norton Rose Fulbright US LLP

(57) ABSTRACT

A device for measuring the quality of an operating substance and/or additive, in particular a reduction agent, stored in a tank, includes a reference container connected to the operating substance and/or the additive via a semi-permeable diaphragm, in which the reference container is filled with a medium which has a known osmotic pressure relative to the used operating substance and/or additive.

10 Claims, 4 Drawing Sheets

(51) Int. Cl.
 *F01N 11/00* (2006.01)
 *G01N 7/10* (2006.01)
 *G01L 19/06* (2006.01)

(52) U.S. Cl.
 CPC .... *F01N 2610/14* (2013.01); *F01N 2610/1406* (2013.01); *F01N 2610/148* (2013.01); *F01N 2900/1818* (2013.01); *Y02T 10/24* (2013.01); *Y02T 10/47* (2013.01)

(56) References Cited

U.S. PATENT DOCUMENTS

| | | | | |
|---|---|---|---|---|
| 4,891,968 A | * | 1/1990 | Steudle | G01N 13/04 73/64.47 |
| 5,141,873 A | * | 8/1992 | Steudle | G01N 13/04 422/82.13 |
| 5,211,055 A | * | 5/1993 | Steudle | G01N 13/04 73/64.47 |
| 6,293,770 B1 | * | 9/2001 | Matsumoto | B01D 35/027 417/313 |
| 2003/0033799 A1 | * | 2/2003 | Scheying | B01D 53/9431 60/286 |
| 2007/0237206 A1 | | 10/2007 | Kubota et al. | |
| 2008/0037908 A1 | * | 2/2008 | Kunstmann | B60K 15/00 383/3 |
| 2009/0320573 A1 | | 12/2009 | Torres et al. | |

FOREIGN PATENT DOCUMENTS

| | | |
|---|---|---|
| DE | 37 36 230 C1 | 3/1989 |
| DE | 103 40 075 A1 | 3/2005 |
| DE | 10 2007 059 853 | 6/2009 |

* cited by examiner

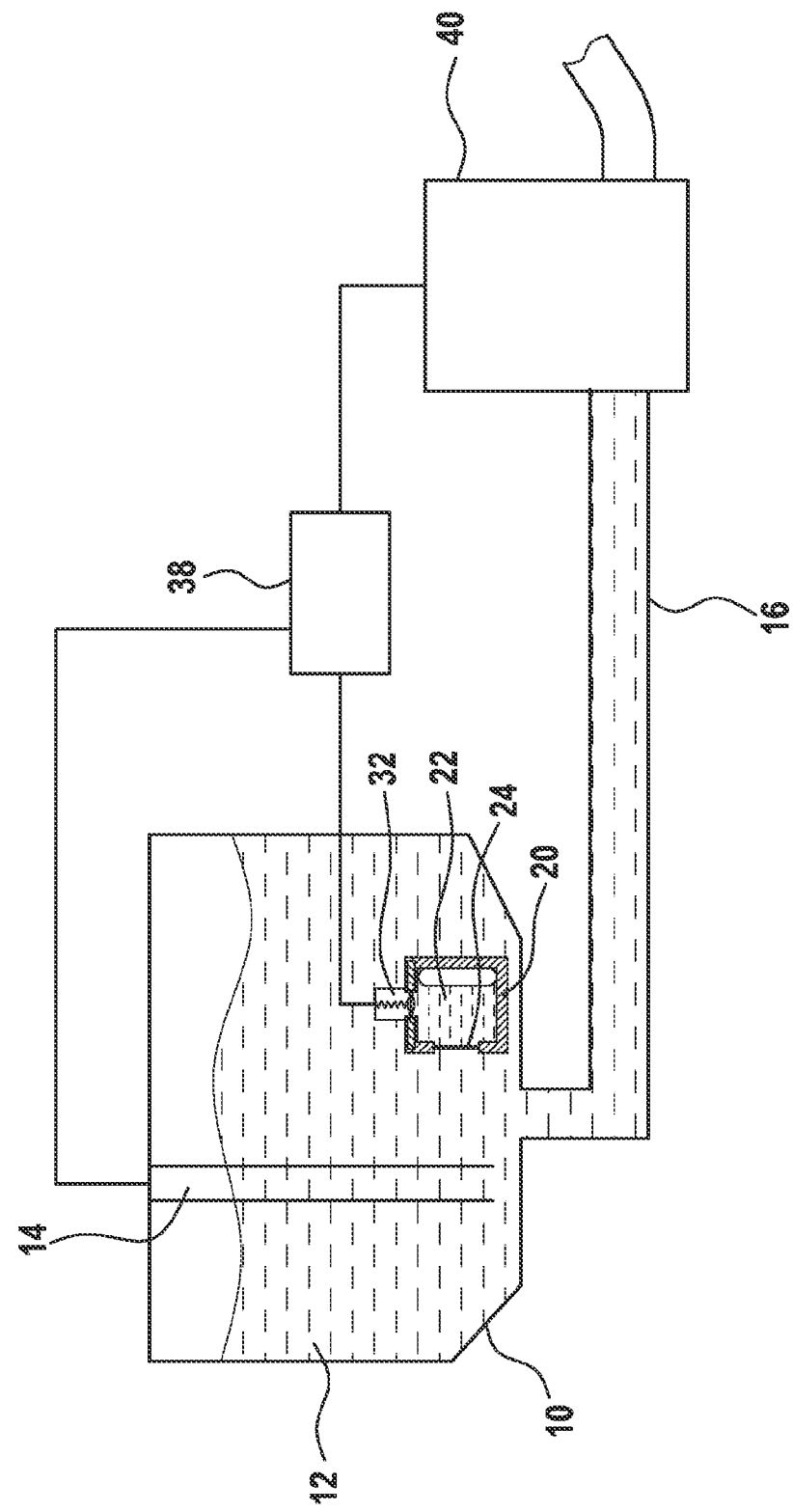

SENSOR FOR DETECTING THE QUALITY OF A FLUID

CROSS REFERENCE TO RELATED APPLICATION

The present application is the national stage entry of International Patent Application No. PCT/EP2012/056186, filed on Apr. 4, 2012, which claims priority to Application No. DE 10 2011 076 496.8, filed in the Federal Republic of Germany on May 26, 2011.

BACKGROUND INFORMATION

In order to comply with the more stringent exhaust gas legislation, nitrogen oxides contained in the exhaust gas must be reduced in internal combustion engines, in particular in self-igniting internal combustion engines. To carry out the necessary exhaust gas aftertreatment, a method based on selective catalytic reduction (SCR) has become very widely accepted. In the SCR method, the nitrogen oxides are reduced into nitrogen and water with the aid of an operating substance and/or additive, in particular a reduction agent. An aqueous urea solution, which is available, for example, under the trade name AdBlue, is often used as the operating substance and/or additive. Thermal decomposition of the urea produces the actual reduction agent, gaseous ammonia, $NH_3$, in the exhaust gas system. The operating substance and/or additive is/are stored in a tank and injected into the exhaust gas system via a delivery or metering module. In this connection, it is always necessary for an adequate amount of reduction agent to be injected by the metering module. To determine the correct amount of the required operating substance and/or additive, the control unit must know the exact properties of the operating substance and/or additive. If the urea content of the frequently used aqueous urea solution is too low, for example, insufficient ammonia is formed in the exhaust gas system and the nitrogen oxides cannot be completely reduced. This has the consequence that the statutory exhaust gas limiting values are exceeded. Causes of an incorrect urea concentration may be, for example, filling an incorrect reduction agent into the tank or deliberately filling the tank with distilled water instead of the operating substance and/or additive due to its significantly lower price. Since the exhaust gas aftertreatment system must ensure compliance with the legal limiting values of nitrogen oxide emissions at all times, it is necessary that the exhaust gas aftertreatment system detects improperly filled operating substances and/or additives, and prevents their use.

German Application No. DE 10 2007 059 853 describes a tank for storing an operating substance or additive, which is equipped with means for measuring the fill level and quality of the liquid in the tank. The measurement is carried out with the aid of an ultrasonic transducer which transmits ultrasonic signals and receives the signals reflected back. From the received ultrasound echoes, it is possible to calculate, among other things, the density of the liquid and the fill level with the aid of the knowledge of the temperature. By comparing the density with stored values, it is possible to infer the nature or quality of the liquid in the tank.

Another approach for determining the quality of the operating substance and/or additive in the tank is to measure the efficiency of the SCR catalyst in reducing nitrogen oxides. The disadvantage of this method is that the discovery of a poor quality of the reduction agent is delayed, i.e., only after it is no longer possible to meet the exhaust gas limiting values, as well as the generally low accuracy of this measurement. All known methods from the related art for measuring the quality of an operating substance and/or additive in a tank exhibit relatively high complexity and expense.

SUMMARY

According to the present invention, a device is described for measuring the quality of an operating substance and/or additive, in particular a reduction agent, stored in a tank, a reference container being connected to the operating substance and/or additive via a semi-permeable membrane, and the reference container being filled with a medium which has a known osmotic pressure relative to the used operating substance and/or additive. The relationship between the osmotic pressure of the concentration of a substance in a solvent compared to a pure solvent and the temperature is described by Van't Hoff's law:

$$P_{osmotic} = c \cdot R \cdot T$$

where
$P_{osmotic}$ is the osmotic pressure,
c is the number of all dissolved, dissociated and undissociated particles present,
R is the universal gas constant, and
T is the temperature in degrees Kelvin.

Depending on the reference medium and tank contents, the osmotic pressure between the medium in the reference container and the operating substance and/or additive in the tank is positive, zero or negative.

In the case of storing a reduction agent for selective catalytic reduction, the operating substance and/or additive is/are, in particular, an aqueous urea solution. An aqueous urea solution having a known concentration of urea may also be used as a reference medium in the reference container. Water is able to diffuse through the semi-permeable diaphragm back and forth between the reference container and the rest of the tank. Depending on the concentration of urea in the reference container and in the rest of the tank, a negative pressure, equal pressure or a positive pressure occurs in the reference container. If, for example, an aqueous urea solution of known concentration is present in the reference container, and if the tank is filled with water instead of the aqueous urea solution, a positive pressure builds up in the reference container by osmosis.

This positive pressure may be ascertained using a pressure sensor attached to the reference container. A control unit which evaluates the signal from the pressure sensor may then take appropriate measures such as reducing the power of the drive or preventing the operation of the internal combustion engine.

In one advantageous exemplary embodiment of the present invention, one or multiple flexible elements are attached to the reference container, which are deformed by the pressure change in the reference container and block the outlet of the tank due to this deformation. This ensures that an improperly filled operating substance and/or additive is/are prevented from entering the exhaust gas system.

A pressure-related deformation, however, could also be used to activate a mechanical element for sealing the tank and/or activating a mechanical switch.

If the reference container is intended to seal the tank outlet via a flexible element, it is advantageous to situate the reference container fixedly in the tank using suitable attachment means. However, if only one signal is generated from the reference container, be it via a pressure sensor or via a mechanical switch attached to the reference container, the reference container may also be situated loosely in the tank.

In another advantageous exemplary embodiment, the reference container is not situated in the tank for storing the operating substance and/or additive itself, but instead in a line leading away from it. In this connection, the reference container is designed to be as small as possible, and is preferably situated at a location that is not readily accessible from the outside. This makes tampering with the reference container difficult.

As a further protection against tampering from the outside but also to make the reference container frost-proof, the container may be reinforced by incorporated metal plates or fibers. It is particularly preferred that one or multiple displacement bodies are installed in the reference container for frost protection in order to be able to absorb an increase in volume caused by freezing contents of the container. In another advantageous exemplary embodiment, the frost protection is ensured by the fact that a reference medium is used having a freezing point below the lowest expected temperature.

In another preferred exemplary embodiment, a dye is added to the reference medium in the reference container, which may be used for easily detecting if the container has been pierced. A piercing of the container would make a pressure equalization between the reference container and the tank possible and thus not allow the quality of the operating substance and/or additive in the tank to be measured. If a reference container, the reference medium of which contains a dye, is pierced, the dye enters the tank contents. The staining of the tank contents, which preferably is also evident as a staining of the exhaust gas of the internal combustion engine, makes it possible to easily detect the tampering. In another exemplary embodiment, the semi-permeable diaphragm of the reference container is designed to rupture when a pressure limit is exceeded. An improper filling would result in a rise in pressure in the reference container which is above the set pressure limit of the semi-permeable diaphragm and the dye contained in the reference medium would be released.

In another preferred exemplary embodiment, measured values from sensors which are usually already present, such as a fill level sensor in the tank or a pressure sensor in the delivery module, are included in the monitoring of the reference container. Sloshing occurring in the tank when the vehicle is moved results in small fluctuations in the fill level of the liquid in the tank, which may also be measured via small pressure fluctuations in the reference container. If these pressure fluctuations are absent in the reference container, this indicates a tampering or a failed sensor. It is further preferred to select the reference medium in the reference container such that a positive or negative pressure permanently occurs in the reference container even when the correct operating substance and/or additive is/are present in the tank. This measured positive or negative pressure in the reference container is used to monitor the operation of the pressure sensor.

Due to its simple design, the device according to the present invention for measuring the quality of an operating substance and/or additive stored in a tank allows a reliable and cost-effective measurement of the quality of the stored operating substance and/or additive. An improper filling is reliably detected and operation of the internal combustion engine with an incorrect or a low quality operating substance and/or additive may be prevented to ensure compliance with the statutory exhaust gas limiting values at all times. The possibility of sealing the tank outlet in the case of improper filling effectively protects the exhaust gas treatment system from possible damage by an improperly filled operating substance and/or additive. The device according to the present invention may be designed to be frost-proof in a simple way by using a temperature-adjusted reference medium and/or displacement bodies, which makes it possible to use the device in regions having low ambient temperatures without great complexity and additional costs. The possible security against tampering of the system in the other exemplary embodiments contributes to increased security compared to the systems known from the related art.

Exemplary embodiments of the present invention are explained in greater detail below with reference to the accompanying drawings.

BRIEF DESCRIPTION OF THE DRAWINGS

FIG. 1 shows a first exemplary embodiment of the device according to the present invention for measuring the quality of an operating substance and/or additive stored in a tank; in this exemplary embodiment, the reference container is situated in the tank.

DETAILED DESCRIPTION

Figure 2A:
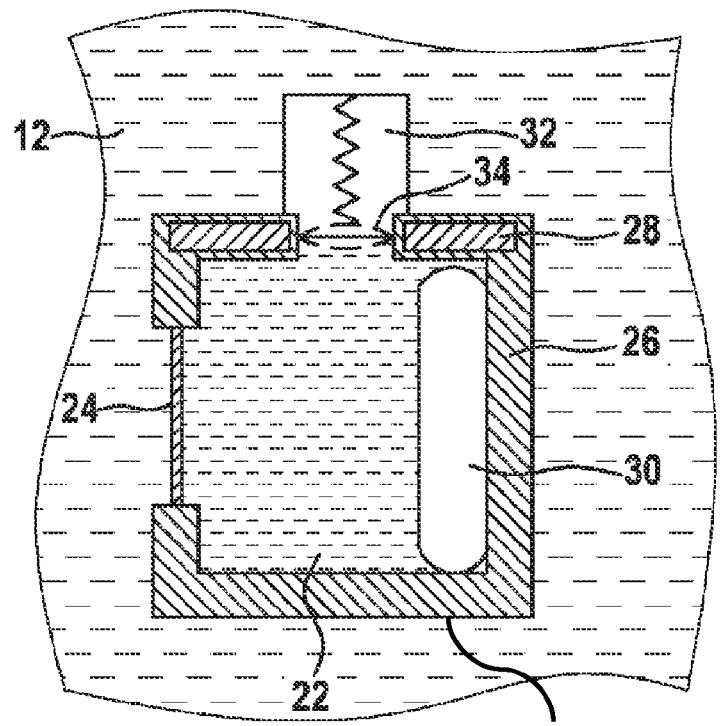
FIG. 2a shows the reference container of the device according to the present invention having a pressure sensor.

A schematic representation of the device for measuring the quality of an operating substance and/or additive stored in a tank is derived from FIG. 1.

FIG. 1 shows a tank 10 for storing an operating substance and/or additive 12. In tank 10 are located a fill level sensor 14 and a reference container 20. The operating substance and/or additive flow(s) via a line 16 to a metering module 40. The reference container has a semi-permeable diaphragm 24, through which water is able to diffuse between the tank and the reference container. The reference container is filled with a reference medium 22. The osmotic pressure occurring between reference container 20 and tank 10 is dependent on operating substance and/or additive 12 in the tank and reference medium 22 used in reference container 20. The pressure in reference container 20 is measured using a pressure sensor 32 and forwarded to a control unit 38. If, for example, both tank 10 and reference container 20 are filled with an aqueous urea solution, both having the same urea concentration, the pressure is equalized. If, for example, tank 10 is now only filled with distilled water instead of an aqueous urea solution, water diffuses through semi-permeable diaphragm 24 from tank 10 into reference container 20 and the pressure in reference container 20 rises. If a limiting value is exceeded, control unit 38 may take suitable measures such as preventing the operation of the internal combustion engine or preventing a liquid which was improperly filled into the tank from being injected into the exhaust gas system by shutting down metering module 40.

FIG. 2a shows a detailed representation of the reference container of the device for measuring the quality of an operating substance and/or additive stored in a tank.

FIG. 2a shows reference container 20, into the wall 26 of which semi-permeable diaphragm 24 has been introduced. If an aqueous urea solution is used, this diaphragm 24 is, for example, permeable for water but not urea. In the interior of reference container 20 is located reference medium 22, which, for example, may also be an aqueous urea solution. Since the eutectic aqueous urea solution, which is normally used, freezes at temperatures below −11° C., reference container 20 is preferably designed to be frost-proof. This may, for example, be carried out using reinforcements of walls 26 or by installing metal plates 28. Walls 26 of reference container 20 may, however, also be reinforced by increasing the wall thickness or by incorporating fibers. The increase in volume occurring when the aqueous urea solution freezes may be compensated for by using a displacement body 30. Displacement body 30 is designed to be elastic and is compressed by the ice. The pressure in reference container 20 is measured by a pressure sensor 32, which is separated from reference medium 22 via a diaphragm 34 in the exemplary embodiment shown in FIG. 2a. If the pressure in reference container 20 is positive, diaphragm 34 is deflected upwards; if the pressure in reference container 20 is negative, it is deflected downwards. Diaphragm 34 prevents a corrosive reference medium 22, such as an aqueous urea solution, from corroding sensor 32. If a sensor 32 which is resistant to reference medium 22 is used, diaphragm 34 may also be omitted.

Figure 2B:
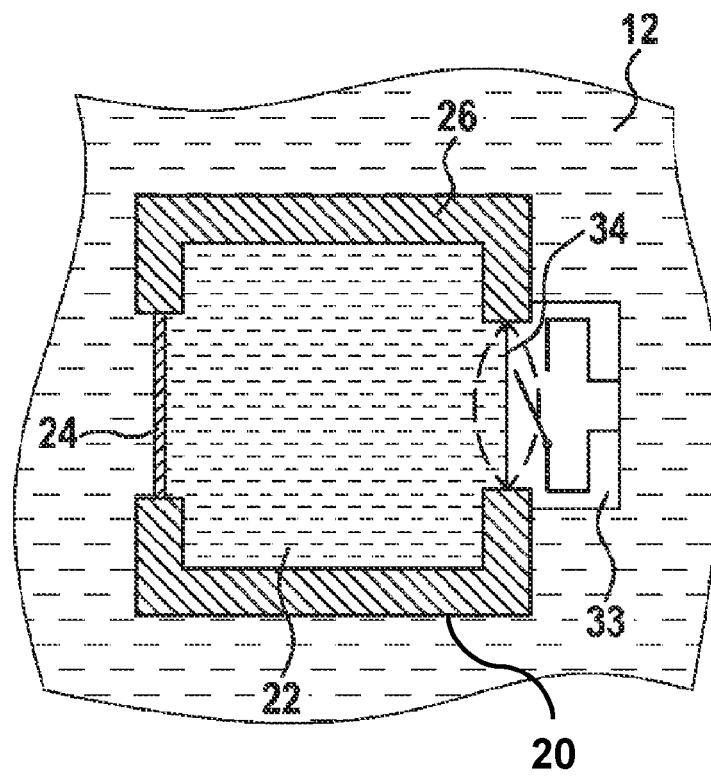
FIG. 2b shows the reference container of the device according to the present invention having a mechanical switch.

FIG. 2b shows a detailed representation of the reference container having a mechanical switch.

FIG. 2b shows reference container 20, into the wall 26 of which semi-permeable diaphragm 24 has been introduced. For the case that an aqueous urea solution is used, this diaphragm 24 is, for example, permeable for water but not urea. Separated by a diaphragm 34 from the interior of reference container 20, a mechanical switch 33 is situated on reference container 20 such that a deflection of diaphragm 34 activates the switch. In the interior of reference container 20 is located reference medium 22, which, for example, may also be an aqueous urea solution. In the case of an aqueous urea solution as operating substance and/or additive 12, the pressure would increase if distilled water was filled into the tank instead of an aqueous urea solution. The positive pressure occurring in the interior of reference container 20 due to filling the improper liquid into the tank deflects diaphragm 34 and hence activates mechanical switch 33. Its signal may be used to take appropriate measures such as reducing the power of the internal combustion engine or preventing its operation.

Figure 3:
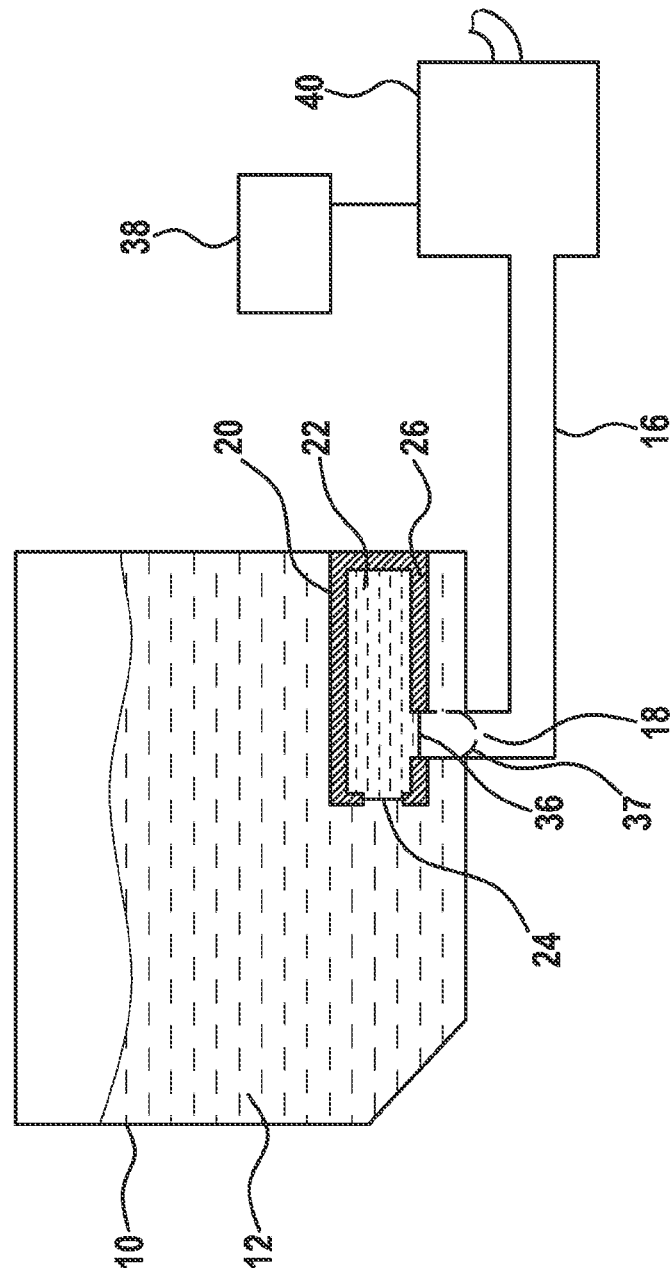
FIG. 3 shows another exemplary embodiment of the device according to the present invention in which the reference container is situated in the tank fixed above the tank outlet using a flexible element.

FIG. 3 shows another exemplary embodiment of the device according to the present invention in which the reference container is equipped with a flexible element.

In the exemplary embodiment of the device according to the present invention shown in FIG. 3 for measuring the quality of an operating substance and/or additive 12 stored in a tank, reference container 20 is fixedly situated in tank 10 above outlet 18 of the tank, via which operating substance and/or additive 12 exit(s) tank 10 and enter(s) line 16. In housing wall 26, reference container 20 has a semi-permeable diaphragm 24, which is designed to be water-permeable if, for example, an aqueous urea solution is used as an operating substance and/or additive 12. An aqueous urea solution may also be used as reference medium 22 in reference container 20. Reference container 20 has at a position located directly above tank outlet 18 a flexible element 36 which may be deformed under pressure. In this example, if only distilled water is filled into the tank instead of an aqueous urea solution as an operating substance and/or additive 12, the pressure increases in reference tank 20 due to osmosis. Due to the increased pressure, flexible element 36 is deformed and assumes the shape indicated in FIG. 3 by reference numeral 37. In this case, tank outlet 18 is blocked by flexible element 36. This prevents an operating substance and/or additive 12 which has/have been improperly pumped into the tank from entering the exhaust gas system via line 16 and metering module 40. Furthermore, control unit 38 is able to detect this error state via sensors already present in metering module 40. Instead of flexible element 36 or 37, tank outlet 18 may also be blocked by a flexible spring element or another mechanical means which is activated by a pressure difference in the reference container.

Figure 4:
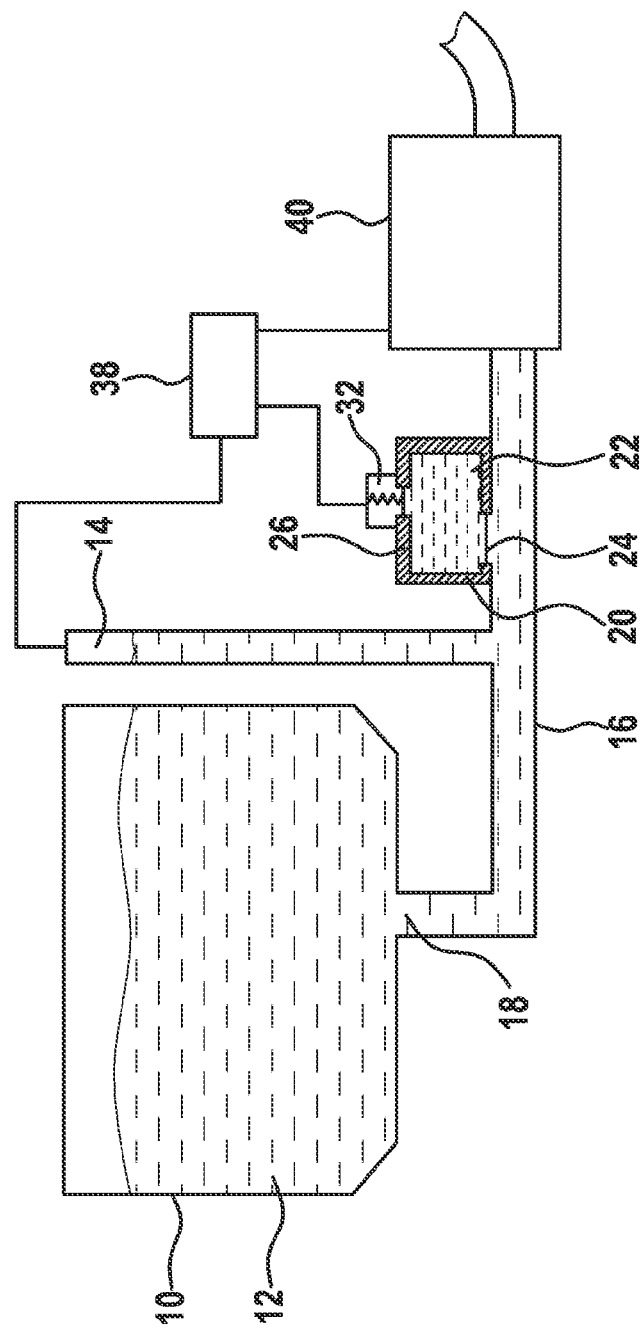
FIG. 4 shows another exemplary embodiment of the device according to the present invention in which the reference container is situated on a line exiting the tank.

FIG. 4 depicts another exemplary embodiment of the device according to the present invention in which the reference container is situated on a line 16 exiting tank 10.

FIG. 4 shows a tank 10 for storing an operating substance and/or additive 12 which flow(s) through tank outlet 18 and line 16 into delivery module 40. A fill level sensor 14 and reference container 20 are situated on line 16. Reference container 20 has a semi-permeable diaphragm 24, which is in direct connection with operating substance and/or additive 12 in line 16. Reference medium 22 is located in the interior of reference container 20. The pressure in the interior of reference container 20 is ascertained by a pressure sensor 32 which, as well as fill level sensor 14, transmits its measured value to a control unit 38. When used in an SCR system, an aqueous urea solution is used, for example, both as operating substance and/or additive 12 as well as reference medium 22. If, for example, tank 10 is improperly filled with distilled water, water diffuses from line 16 into the interior of reference container 20 and causes the pressure in the interior to increase. If the increase in pressure measured by sensor 32 exceeds a critical limiting value, control unit 38 may take suitable measures such as preventing the injection of an improperly filled operating substance and/or additive 12 into the exhaust gas treatment system by shutting down delivery module 40. In order to verify the plausibility of the pressure values delivered by pressure sensor 32, i.e., securing against tampering and/or failure of one or multiple sensors, control unit 38 may use additional data sources, such as fill level sensor 14 or sensors built into delivery module 40. For example, movements of operating substance and/or additive 12 in tank 10, which are detected by fill level sensor 14, also result in minor pressure fluctuations which are detected by sensor 32. Control unit 38 may combine the measured values from both sensors and infer the failure of and/or tampering with one of the sensors from the absence of pressure fluctuations or fill level fluctuations. Another possibility for verifying the sensor data in an SCR system using an aqueous urea solution is to use as reference medium 22 an aqueous urea solution having a changed urea concentration compared to the solution present in tank 10. In the case of a proper filling of tank 10, this also results in a positive pressure or negative pressure in reference container 20 which must be detected by the sensor 32. A failure of detection of the positive pressure or negative pressure indicates a tampering with sensor 32 or reference container 20. For example, a pierced reference container 20 would allow an unimpeded exchange of liquid between the interior of reference container 20 and tank 10, making it impossible for a pressure difference to occur in any case. To prevent tampering with reference container 20, it is advantageous to reinforce container walls 26, for example by incorporating metal plates 28, and/or to place reference container 20 at a position where access from the outside is very difficult. It is also advantageous to design reference container 20 to be as small as possible, since this makes it very difficult to access from the outside. A piercing of reference container 20 may be verified in one exemplary embodiment, for example, by adding a dye to reference medium 22. If reference container 20 was pierced, dye would pass from the interior of reference container 20 into tank 10 or line 16 and stain tank contents 12. This staining is preferably also detectable in the exhaust gas.

What is claimed is:

1. A device for measuring a quality of an operating substance, additive and/or reduction agent, stored in a tank, comprising:
    a reference container connected to the operating substance, additive and/or reduction agent via a semi-permeable diaphragm,
    wherein the reference container is filled with a medium having a known osmotic pressure relative to the operating substance, additive and/or reduction agent, and
    wherein a pressure change in the reference container deforms at least one flexible elements such that the at least one flexible element seals a tank outlet of the tank.

2. The device according to claim 1, wherein the osmotic pressure between the medium in the reference container and the operating substance, additive and/or reduction agent in the tank is positive, zero or negative.

3. The device according to claim 1, further comprising:
    a device for measuring the pressure situated in the reference container.

4. The device according to claim 1, wherein pressure-related deformations in the reference container activate a mechanical element.

5. The device according to claim 1, wherein the reference container is situated loosely within the tank or is fixed using an attachment device.

6. The device according to claim 1, wherein the reference container is situated in a line exiting the tank.

7. The device according to claim 1, wherein walls of the reference container are reinforced by thickened walls, incorporated metal plates and/or fibers.

8. The device according to claim 1, wherein the medium in an interior of the reference container is provided with a dye.

9. A method for measuring a quality of an operating substance, additive and/or reduction agent, stored in a tank, comprising:
    performing a measurement using pressure and/or a pressure curve in a reference container, which is connected to the operating substance, additive and/or reduction agent via a semi-permeable diaphragm, and
    wherein a pressure change in the reference container deforms at least one flexible elements such that the at least one flexible element seals a tank outlet of the tank.

10. The method according to claim 9, further comprising:
    verifying a plausibility of measured values from the reference container via measurements of a fill level and/or by a positive pressure, equal pressure or negative pressure occurring in the reference container.

* * * * *